(12) United States Patent
Andersohn et al.

(10) Patent No.: US 7,680,522 B2
(45) Date of Patent: Mar. 16, 2010

(54) METHOD AND APPARATUS FOR DETECTING MISAPPLIED SENSORS

(75) Inventors: Lutz Andersohn, Oakland, CA (US); Pete Andriola, Alamo, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 290 days.

(21) Appl. No.: 11/541,301

(22) Filed: Sep. 29, 2006

(65) Prior Publication Data
US 2008/0081967 A1 Apr. 3, 2008

(51) Int. Cl.
*A61B 5/145* (2006.01)
(52) U.S. Cl. .................... 600/310; 600/323
(58) Field of Classification Search ........ 600/310, 600/323, 344
See application file for complete search history.

(56) References Cited

U.S. PATENT DOCUMENTS

| | | |
|---|---|---|
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |

(Continued)

FOREIGN PATENT DOCUMENTS

DE 3516338 11/1986

(Continued)

OTHER PUBLICATIONS

U.S. Appl. No. 11/507,814, filed Aug. 22, 2006, Baker, Jr.

(Continued)

*Primary Examiner*—Eric F Winakur
*Assistant Examiner*—Etsub D Berhanu
(74) *Attorney, Agent, or Firm*—Fletcher Yoder

(57) ABSTRACT

A method and system are provided for determining whether a spectrophotometric sensor is misapplied. In one embodiment, a spectrophotometric sensor is provided with a strain sensor configures to provide a signal related to the curvature of the spectrophotometric sensor. In such an embodiment, the signal may be compared, such as by an associated monitor, with an expected signal value. Based upon this comparison, a determination may be made whether or not the spectrophotometric sensor is misapplied.

23 Claims, 7 Drawing Sheets

U.S. PATENT DOCUMENTS

| | | | |
|---|---|---|---|
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hansmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,035,243 A | 7/1991 | Muz | |
| 5,040,539 A | 8/1991 | Schmitt et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,084,327 A | 1/1992 | Stengel | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H1039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,962 A | 6/1993 | Mannheimer et al. | |
| 5,224,478 A | 7/1993 | Sakai et al. | |
| 5,226,417 A * | 7/1993 | Swedlow et al. | 600/336 |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Friedman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,273,036 A | 12/1993 | Kronberg et al. | |
| 5,275,159 A | 1/1994 | Griebel | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Friedman et al. | |
| 5,311,865 A | 5/1994 | Mayeux | |
| 5,313,940 A | 5/1994 | Fuse et al. | |
| 5,323,776 A | 6/1994 | Blakely et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub et al. | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,361,758 A | 11/1994 | Hall et al. | |
| 5,365,066 A | 11/1994 | Krueger, Jr. et al. | |
| 5,368,025 A | 11/1994 | Young et al. | |
| 5,368,026 A | 11/1994 | Swedlow et al. | |
| 5,368,224 A | 11/1994 | Richardson et al. | |
| 5,372,136 A | 12/1994 | Steuer et al. | |
| 5,377,675 A | 1/1995 | Ruskewicz et al. | |
| 5,385,143 A | 1/1995 | Aoyagi | |
| 5,387,122 A | 2/1995 | Goldberger et al. | |
| 5,390,670 A | 2/1995 | Centa et al. | |
| 5,392,777 A | 2/1995 | Swedlow et al. | |
| 5,398,680 A | 3/1995 | Polson et al. | |
| 5,402,777 A | 4/1995 | Warring et al. | |
| 5,411,023 A | 5/1995 | Morris, Sr. et al. | |
| 5,411,024 A | 5/1995 | Thomas et al. | |
| 5,413,099 A | 5/1995 | Schmidt et al. | |
| 5,413,100 A | 5/1995 | Barthelemy et al. | |
| 5,413,101 A | 5/1995 | Sugiura | |
| 5,413,102 A | 5/1995 | Schmidt et al. | |

| Patent No. | Date | Name |
|---|---|---|
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,474,065 A | 12/1995 | Meathrel et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |

| | | | | | | |
|---|---|---|---|---|---|---|
| 5,860,919 | A | 1/1999 | Kiani-Azarbayjany et al. | 6,083,157 A | 7/2000 | Noller |
| 5,865,736 | A | 2/1999 | Baker, Jr. et al. | 6,083,172 A | 7/2000 | Baker, Jr. et al. |
| 5,871,442 | A | 2/1999 | Madarasz et al. | 6,088,607 A | 7/2000 | Diab et al. |
| 5,879,294 | A | 3/1999 | Anderson et al. | 6,094,592 A | 7/2000 | Yorkey et al. |
| 5,885,213 | A | 3/1999 | Richardson et al. | 6,095,974 A | 8/2000 | Shemwell et al. |
| 5,890,929 | A | 4/1999 | Mills et al. | 6,104,938 A | 8/2000 | Huiku et al. |
| 5,891,021 | A | 4/1999 | Dillon et al. | 6,112,107 A | 8/2000 | Hannula |
| 5,891,022 | A | 4/1999 | Pologe | 6,113,541 A | 9/2000 | Dias et al. |
| 5,891,024 | A | 4/1999 | Jarman et al. | 6,115,621 A | 9/2000 | Chin |
| 5,891,025 | A | 4/1999 | Buschmann et al. | 6,122,535 A | 9/2000 | Kaestle et al. |
| 5,891,026 | A | 4/1999 | Wang et al. | 6,133,994 A | 10/2000 | Mathews et al. |
| 5,902,235 | A | 5/1999 | Lewis et al. | 6,135,952 A | 10/2000 | Coetzee |
| 5,910,108 | A | 6/1999 | Solenberger | 6,144,444 A | 11/2000 | Haworth et al. |
| 5,911,690 | A | 6/1999 | Rall | 6,144,867 A | 11/2000 | Walker et al. |
| 5,912,656 | A | 6/1999 | Tham et al. | 6,144,868 A | 11/2000 | Parker |
| 5,913,819 | A | 6/1999 | Taylor et al. | 6,149,481 A | 11/2000 | Wang et al. |
| 5,916,154 | A | 6/1999 | Hobbs et al. | 6,150,951 A | 11/2000 | Olejniczak |
| 5,916,155 | A | 6/1999 | Levinson et al. | 6,151,107 A | 11/2000 | Schöllerman et al. |
| 5,919,133 | A | 7/1999 | Taylor et al. | 6,151,518 A | 11/2000 | Hayashi |
| 5,919,134 | A | 7/1999 | Diab | 6,152,754 A | 11/2000 | Gerhardt et al. |
| 5,920,263 | A | 7/1999 | Huttenhoff et al. | 6,154,667 A | 11/2000 | Miura et al. |
| 5,921,921 | A | 7/1999 | Potratz et al. | 6,157,850 A | 12/2000 | Diab et al. |
| 5,922,607 | A | 7/1999 | Bernreuter | 6,163,715 A | 12/2000 | Larsen et al. |
| 5,924,979 | A | 7/1999 | Swedlow et al. | 6,165,005 A | 12/2000 | Mills et al. |
| 5,924,980 | A | 7/1999 | Coetzee | 6,173,196 B1 | 1/2001 | Delonzor et al. |
| 5,924,982 | A | 7/1999 | Chin | 6,178,343 B1 | 1/2001 | Bindszus et al. |
| 5,924,985 | A | 7/1999 | Jones | 6,181,958 B1 | 1/2001 | Steuer et al. |
| 5,934,277 | A | 8/1999 | Mortz | 6,181,959 B1 | 1/2001 | Schöllerman et al. |
| 5,934,925 | A | 8/1999 | Tobler et al. | 6,184,521 B1 | 2/2001 | Coffin, IV et al. |
| 5,940,182 | A | 8/1999 | Lepper, Jr. et al. | 6,188,470 B1 | 2/2001 | Grace |
| 5,954,644 | A | 9/1999 | Dettling et al. | 6,192,260 B1 | 2/2001 | Chance |
| 5,960,610 | A | 10/1999 | Levinson et al. | 6,195,575 B1 | 2/2001 | Levinson |
| 5,961,450 | A | 10/1999 | Merchant et al. | 6,198,951 B1 | 3/2001 | Kosuda et al. |
| 5,961,452 | A | 10/1999 | Chung et al. | 6,206,830 B1 | 3/2001 | Diab et al. |
| 5,964,701 | A | 10/1999 | Asada et al. | 6,213,952 B1 | 4/2001 | Finarov et al. |
| 5,971,930 | A | 10/1999 | Elghazzawi | 6,217,523 B1 | 4/2001 | Amano et al. |
| 5,978,691 | A | 11/1999 | Mills | 6,222,189 B1 | 4/2001 | Misner et al. |
| 5,978,693 | A | 11/1999 | Hamilton et al. | 6,226,539 B1 | 5/2001 | Potratz |
| 5,983,122 | A | 11/1999 | Jarman et al. | 6,226,540 B1 | 5/2001 | Bernreuter et al. |
| 5,987,343 | A | 11/1999 | Kinast | 6,229,856 B1 | 5/2001 | Diab et al. |
| 5,991,648 | A | 11/1999 | Levin | 6,230,035 B1 | 5/2001 | Aoyagi et al. |
| 5,995,855 | A | 11/1999 | Kiani et al. | 6,233,470 B1 | 5/2001 | Tsuchiya |
| 5,995,856 | A | 11/1999 | Mannheimer et al. | 6,236,871 B1 | 5/2001 | Tsuchiya |
| 5,995,858 | A | 11/1999 | Kinast | 6,236,872 B1 | 5/2001 | Diab et al. |
| 5,995,859 | A | 11/1999 | Takahashi | 6,240,305 B1 | 5/2001 | Tsuchiya |
| 5,997,343 | A | 12/1999 | Mills et al. | 6,253,097 B1 | 6/2001 | Aronow et al. |
| 5,999,834 | A | 12/1999 | Wang et al. | 6,253,098 B1 | 6/2001 | Walker et al. |
| 6,002,952 | A | 12/1999 | Diab et al. | 6,256,523 B1 | 7/2001 | Diab et al. |
| 6,005,658 | A | 12/1999 | Kaluza et al. | 6,256,524 B1 | 7/2001 | Walker et al. |
| 6,006,120 | A | 12/1999 | Levin | 6,261,236 B1 | 7/2001 | Grimblatov |
| 6,011,985 | A | 1/2000 | Athan et al. | 6,263,221 B1 | 7/2001 | Chance et al. |
| 6,011,986 | A | 1/2000 | Diab et al. | 6,263,222 B1 | 7/2001 | Diab et al. |
| 6,014,576 | A | 1/2000 | Raley et al. | 6,263,223 B1 | 7/2001 | Shepherd et al. |
| 6,018,673 | A | 1/2000 | Chin et al. | 6,266,546 B1 | 7/2001 | Steuer et al. |
| 6,018,674 | A | 1/2000 | Aronow | 6,266,547 B1 | 7/2001 | Walker et al. |
| 6,022,321 | A | 2/2000 | Amano et al. | 6,272,363 B1 | 8/2001 | Casciani et al. |
| 6,023,541 | A | 2/2000 | Merchant et al. | 6,278,522 B1 | 8/2001 | Lepper, Jr. et al. |
| 6,026,312 | A | 2/2000 | Shemwell et al. | 6,280,213 B1 | 8/2001 | Tobler et al. |
| 6,026,314 | A | 2/2000 | Amerov et al. | 6,280,381 B1 | 8/2001 | Malin et al. |
| 6,031,603 | A | 2/2000 | Fine et al. | 6,285,894 B1 | 9/2001 | Oppelt et al. |
| 6,035,223 | A | 3/2000 | Baker, Jr. | 6,285,895 B1 | 9/2001 | Ristolainen et al. |
| 6,036,642 | A | 3/2000 | Diab et al. | 6,285,896 B1 | 9/2001 | Tobler et al. |
| 6,041,247 | A | 3/2000 | Weckstrom et al. | 6,298,252 B1 | 10/2001 | Kovach et al. |
| 6,044,283 | A | 3/2000 | Fein et al. | 6,308,089 B1 | 10/2001 | Von der Ruhr et al. |
| 6,047,201 | A | 4/2000 | Jackson, III | 6,321,100 B1 | 11/2001 | Parker |
| 6,061,584 | A | 5/2000 | Lovejoy et al. | 6,330,468 B1 | 12/2001 | Scharf |
| 6,064,898 | A | 5/2000 | Aldrich | 6,334,065 B1 | 12/2001 | Al-Ali et al. |
| 6,064,899 | A | 5/2000 | Fein et al. | 6,339,715 B1 | 1/2002 | Bahr et al. |
| 6,067,462 | A | 5/2000 | Diab et al. | 6,343,223 B1 | 1/2002 | Chin et al. |
| 6,073,038 | A | 6/2000 | Wang et al. | 6,343,224 B1 | 1/2002 | Parker |
| 6,078,833 | A | 6/2000 | Hueber | 6,349,228 B1 | 2/2002 | Kiani et al. |
| 6,081,735 | A | 6/2000 | Diab et al. | 6,351,658 B1 | 2/2002 | Middleman et al. |
| 6,081,742 | A | 6/2000 | Amano et al. | 6,353,750 B1 | 3/2002 | Kimura et al. |

| | | |
|---|---|---|
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B2 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |

| Patent | Date | Inventor |
|---|---|---|
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,811,538 B2 | 11/2004 | Westbrook et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | Zhu et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,039,538 B2 | 5/2006 | Baker, Jr. |
| 7,043,289 B2 | 5/2006 | Fine et al. |
| 7,047,055 B2 | 5/2006 | Boaz et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,072,703 B2 | 7/2006 | Zhang et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,194,293 B2 | 3/2007 | Baker, Jr. |
| 7,198,778 B2 | 4/2007 | Achilefu et al. |
| 7,209,774 B2 | 4/2007 | Baker, Jr. |
| 7,209,775 B2 | 4/2007 | Bae et al. |
| 7,215,984 B2 | 5/2007 | Diab et al. |
| 7,215,991 B2 | 5/2007 | Besson et al. |
| 7,225,006 B2 | 5/2007 | Al-Ali et al. |
| 7,236,811 B2 | 6/2007 | Schmitt |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Schmid |
| 7,277,741 B2 | 10/2007 | Debreczeny et al. |
| 7,280,858 B2 | 10/2007 | Al-Ali et al. |
| 7,289,837 B2 | 10/2007 | Mannheimer et al. |
| 7,295,866 B2 | 11/2007 | Al-Ali et al. |
| 7,297,119 B2 | 11/2007 | Westbrook et al. |
| 7,302,284 B2 | 11/2007 | Baker, Jr. et al. |
| 7,305,262 B2 | 12/2007 | Brodnick et al. |
| 7,315,753 B2 | 1/2008 | Baker, Jr. et al. |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |

| | | |
|---|---|---|
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1* | 10/2003 | Fein et al. .................. 600/323 |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0027207 A1 | 2/2005 | Westbrook et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0085735 A1 | 4/2005 | Baker, Jr. et al. |
| 2005/0113651 A1 | 5/2005 | Wood et al. |
| 2005/0143634 A1 | 6/2005 | Baker, Jr. et al. |
| 2005/0177034 A1 | 8/2005 | Beaumont |
| 2005/0197548 A1 | 9/2005 | Dietiker |
| 2005/0197552 A1 | 9/2005 | Baker, Jr. |
| 2005/0197579 A1 | 9/2005 | Baker, Jr. |
| 2005/0197793 A1 | 9/2005 | Baker, Jr. |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0030764 A1 | 2/2006 | Porges et al. |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0135860 A1 | 6/2006 | Baker, Jr. et al. |
| 2006/0183988 A1 | 8/2006 | Baker, Jr. et al. |
| 2006/0195028 A1 | 8/2006 | Hannula et al. |
| 2006/0200015 A1 | 9/2006 | Baker, Jr. |
| 2006/0224058 A1 | 10/2006 | Mannheimer |
| 2006/0247501 A1 | 11/2006 | Ali |
| 2006/0253016 A1 | 11/2006 | Baker, Jr. et al. |
| 2006/0258921 A1 | 11/2006 | Addison et al. |
| 2006/0264726 A1 | 11/2006 | Mannheimer et al. |
| 2006/0264727 A1 | 11/2006 | Mannheimer et al. |
| 2006/0276700 A1 | 12/2006 | O'Neil |
| 2006/0281984 A1 | 12/2006 | Mannheimer et al. |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0068527 A1 | 3/2007 | Baker, Jr. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2007/0077200 A1 | 4/2007 | Baker, Jr. |
| 2007/0078316 A1* | 4/2007 | Hoarau et al. ............... 600/323 |
| 2007/0100220 A1 | 5/2007 | Baker, Jr. |
| 2007/0106137 A1 | 5/2007 | Baker, Jr. et al. |
| 2007/0118027 A1 | 5/2007 | Baker, Jr. et al. |
| 2007/0179369 A1 | 8/2007 | Baker, Jr. |
| 2007/0208235 A1 | 9/2007 | Besson et al. |

2007/0208242 A1    9/2007    Baker, Jr.

FOREIGN PATENT DOCUMENTS

| | | |
|---|---|---|
| DE | 3703458 | 8/1988 |
| DE | 19632361 | 2/1997 |
| EP | 0127947 | 12/1984 |
| EP | 0204259 | 12/1986 |
| EP | 0531631 | 3/1993 |
| EP | 0724860 | 8/1996 |
| FR | 2685865 | 7/1993 |
| JP | 2111343 | 4/1990 |
| JP | 3116259 | 12/1991 |
| JP | 3116260 | 12/1991 |
| JP | 5049625 | 3/1993 |
| JP | 6014906 | 1/1994 |
| JP | 6269430 | 9/1994 |
| JP | 7001273 | 1/1995 |
| JP | 7236625 | 9/1995 |
| JP | 2000237170 | 9/2000 |
| JP | 2003275192 | 9/2003 |
| JP | 2004089546 | 3/2004 |
| JP | 2004159810 | 6/2004 |
| JP | 2004329406 | 11/2004 |
| JP | 2004337605 | 12/2004 |
| JP | 2004344367 | 12/2004 |
| JP | 2004351107 | 12/2004 |
| WO | WO8909566 | 10/1989 |
| WO | WO9001293 | 2/1990 |
| WO | WO9111137 | 8/1991 |
| WO | WO9502358 | 1/1995 |
| WO | WO9639927 | 12/1996 |
| WO | WO9736536 | 10/1997 |
| WO | WO9857577 | 12/1998 |
| WO | WO9947039 | 9/1999 |
| WO | WO0059374 | 10/2000 |
| WO | WO2005010567 | 2/2005 |
| WO | WO2005010568 | 2/2005 |
| WO | WO2007141121 | 12/2007 |

OTHER PUBLICATIONS

U.S. Appl. No. 11/524,182, filed Sep. 20, 2006, Baker, Jr., et al.
U.S. Appl. No. 11/528,295, filed Sep. 27, 2006, Baker, Jr.
U.S. Appl. No. 11/528,218, filed Sep. 27, 2006, Campbell, et al.
U.S. Appl. No. 11/528,154, filed Sep. 27, 2006, Debreczeny, et al.
U.S. Appl. No. 11/528,862, filed Sep. 28, 2006, Baker, Jr.
Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).
Izumi, Akio, et al.; "Accuracy and Utility of a New Reflectance Pulse Oximeter for Fetal Monitoring During Labor," *Journal of Clinical Monitoring*, vol. 13, pp. 103-108 (1997).
"Smaller Product, Tighter Tolerances Pose Dispensing Challenges for Medical Device Manufacturer," *Adhesives Age*, pp. 40-41 (Oct. 1997).
Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.
DeKock, Marc; "Pulse Oximetry Probe Adhesive Disks: a Potential for Infant Aspiration," *Anesthesiology*, vol. 89, pp. 1603-1604 (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1919.
Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.
Ferrell, T.L., et al.; "Medical Telesensors," *SPIE*, vol. 3253, pp. 193-198 (1998).
Yang, Boo-Ho, et al.; "Development of the ring sensor for healthcare automation," *Robotics and Autonomous Systems*, vol. 30, pp. 273-281 (2000).
Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.
Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.
Schulz, Christian Eric; "Design of a Pulse Oximetry Sensor Housing Assembly," California State University Master's Thesis, *UMI Dissertation Services*, UMI No. 1401306, (May 2000) 63 pages.
Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.
Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).
Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).
Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).
Earthrowl-Gould, T., et al.; "Chest and abdominal surface motion measurement for continuous monitoring of respiratory function," *Proc. Instn Mech Engrs*, V215, Part H; pp. 515-520 (2001).
Irie, A., et al.; "Respiration Monitors—Pulse Oximeters," *Neonatal Care*, vol. 15, No. 12, pp. 78-83 (2002) (Article in Japanese—contains English summary of article).
Shaltis, Phillip, et al.; "Implementation and Validation of a Power-Efficient, High-Speed Modulation Design for Wireless Oxygen Saturation Measurement Systems," *IEEE*, pp. 193-194 (2002).
Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.
Matsui, A., et al.; "Pulse Oximeter," *Neonatal Care*, vol. 16, No. 3, pp. 38-45 (2003) (Article in Japanese—contains English summary of article).
Nakagawa, M., et al.; "Oxygen Saturation Monitor," *Neonatal Monitoring*, vol. 26, No. 5, pp. 536-539 (2003) (Article in Japanese—contains English summary of article).
Urquhart, C., et al.; "Ear probe pulse oximeters and neonates," *Anaesthesia*, vol. 60, p. 294 (2005).
Bentley, David J. et al.; "Measure Pressure with Thin Film"; Paper Film & Foil Converter; May 1, 2003.

* cited by examiner

METHOD AND APPARATUS FOR DETECTING MISAPPLIED SENSORS

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Sensors exist that are designed to be applied to different areas on a patient, such as the forehead, nose, or digits. To facilitate accurate and reliable measurements when monitoring physiological characteristics of a patient, a sensor should be properly applied to the area for which it was designed. That is, a digit sensor that is improperly applied to a patient's forehead, as is often observed in a clinical setting, may produce inaccurate results due to its improper placement.

SUMMARY

Certain aspects commensurate in scope with the claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a spectrophotometric sensor including: a sensor body; an emitter and a detector disposed on the sensor body; and a strain sensor disposed on the sensor body, wherein the strain sensor is configured to provide a signal related to a curvature of the spectrophotometric sensor.

There is also provided a system including: a monitor; and a spectrophotometric sensor adapted to be operatively coupled to the monitor, where the sensor includes: a sensor body; an emitter and a detector disposed on the sensor body; and a strain sensor disposed on the sensor body, wherein the strain sensor is configured to provide a signal related to a curvature of the spectrophotometric sensor.

There is also provided a method of manufacturing a sensor, including: providing an optical package in which an emitter and a detector are disposed; combining the optical package and a strain sensor such that a signal related to a curvature of the optical package can be measured; and disposing the strain sensor and the optical package on a sensor body.

There is also provided a method for detecting a misapplied sensor, including: receiving a signal related to a curvature of a spectrophotometric sensor at a monitor; comparing the signal with a threshold signal value; and providing a notification if the comparison indicates that the spectrophotometric sensor is misapplied.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present technique, medical sensors for pulse oximetry or other applications utilizing spectrophotometry are provided that may provide a signal related to the misapplication of the sensor. As provided herein, the spectrophotometric sensors may include one or more strain sensors in accordance with embodiments of the present technique. Such strain sensors may relay a signal to a downstream medical device in order to convey an incorrect application of the spectrophotometric sensor to a healthcare practitioner, for example when a digit sensor is placed on a patient's forehead. By providing information related to the correct placement of a spectrophotometric sensor, strain sensors as provided herein may reduce measurement errors that may result from a spectrophotometric sensor being applied improperly.

Figure 1:
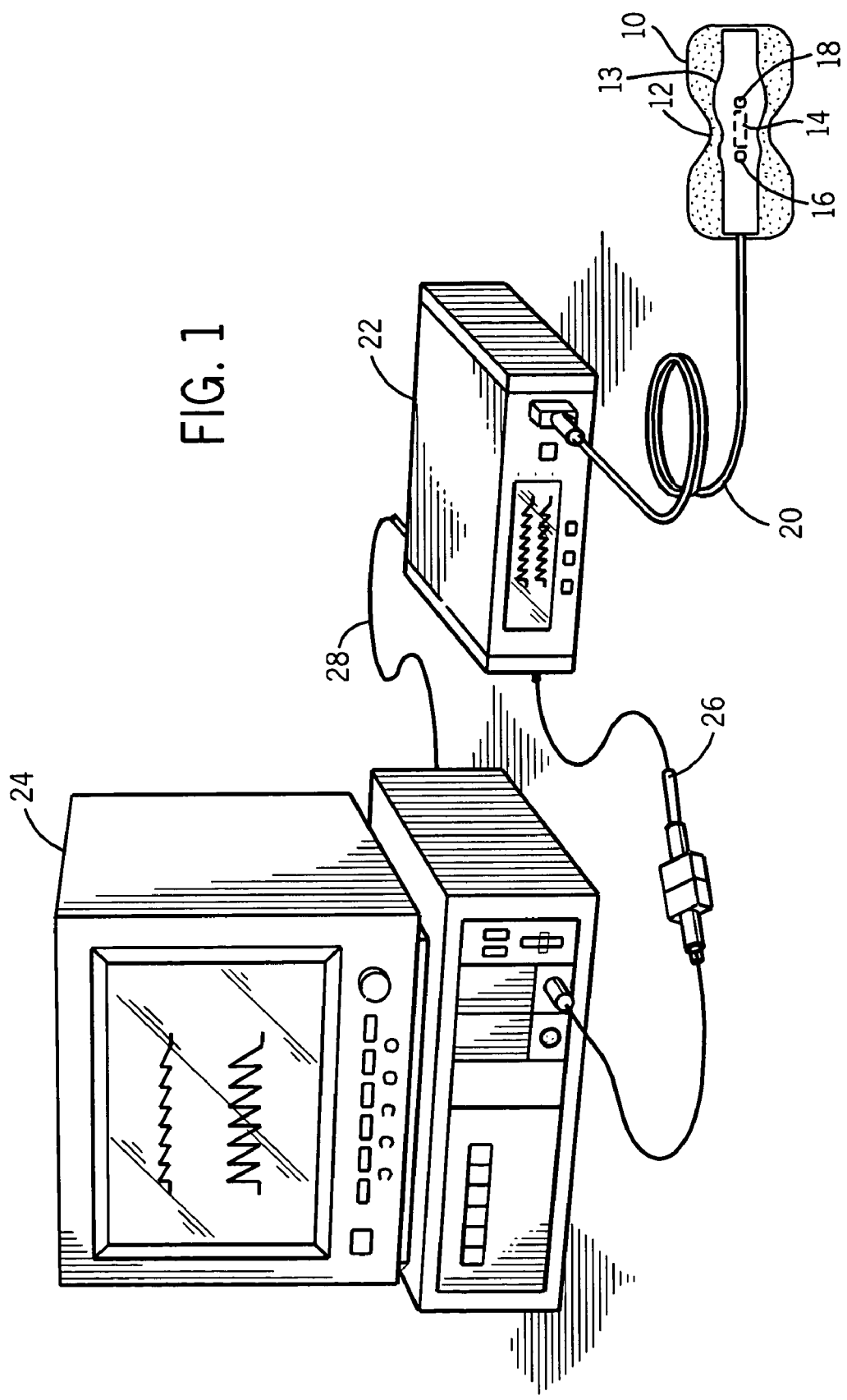
FIG. 1 illustrates a pulse oximetry system coupled to a multi-parameter patient monitor and a sensor according to aspects of the present technique.

FIG. 1 illustrates a spectrophotometric sensor 10 used in conjunction with a downstream medical device, which may include a pulse oximetry monitor 22. Spectrophotometric sensor 10 may include a sensor body 12, a flexible optical package 13 and a strain sensor 14. It should be appreciated that the optical package 13 may include an emitter 16 and a detector 18. In addition, as discussed below with reference to FIG. 6, the optical package may also include the strain sensor 14 in certain embodiments. Alternatively, the strain sensor 14 may be a separate component from the optical package 13 on the spectrophotometric sensor 10.

The optical package 13 may be disposed on a sensor body 12, which may be made of any suitable material, such as plastic, foam, woven material, or paper. In the depicted embodiments, the spectrophotometric sensor 10 is coupled to a cable 20 that is responsible for transmitting electrical and/or optical signals to and from the strain sensor 14, the emitter 16 and the detector 18. The cable 20 may be permanently coupled to the spectrophotometric sensor 10, or it may be removably coupled to the spectrophotometric sensor 10, the latter alternative being more useful and cost efficient in situations where the spectrophotometric sensor 10 is disposable. It should be appreciated that the cable 20 of the spectrophotometric sensor 10 may be coupled to the monitor 22 or it may be coupled to a transmission device (not shown) to facilitate wireless transmission between the spectrophotometric sensor 10 and the monitor 22. In an exemplary embodiment, the monitor 22 may be any suitable pulse oximeter, such as those available from Nellcor Puritan Bennett Inc. Furthermore, to upgrade conventional pulse oximetry provided by the monitor 22 to provide additional functions, the monitor 22 may be coupled to a multi-parameter patient monitor 24 via a cable 26 connected to a sensor input port or via a cable 28 connected to a digital communication port.

The emitter 16 and the detector 18 may be of any suitable type. For example, the emitter 16 may be one or more light emitting diodes adapted to transmit one or more wavelengths of light, and the detector 18 may be one or more photodetectors selected to receive light in the range or ranges emitted from the emitter 16. Alternatively, the emitter 16 may also be a laser diode or a vertical cavity surface emitting laser (VCSEL). The emitter 16 and the detector 18 may also include optical fiber sensing elements. The emitter 16 may include a broadband or "white light" source, in which case the detector could include any of a variety of elements for selecting specific wavelengths, such as reflective or refractive elements or interferometers. These kinds of emitters and/or detectors would typically be coupled to the spectrophotometric sensor via fiber optics. Alternatively, a spectrophotometric sensor 10 may sense light detected from the tissue at a different wavelength from the light emitted into the tissue. Such sensors may be adapted to sense fluorescence, phosphorescence, Raman scattering, Rayleigh scattering and multi-photon events or photoacoustic effects. For pulse oximetry applications using either transmission or reflectance type spectrophotometric sensors the oxygen saturation of the patient's arterial blood may be determined using two or more wavelengths of light, most commonly red and near infrared wavelengths. Similarly, in other applications, a tissue water fraction (or other tissue constituent related metric) or a concentration of one or more biochemical components in an aqueous environment may be measured using two or more wavelengths of light. In certain embodiments, these wavelengths may be infrared wavelengths between about 1,000 nm and about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present techniques.

The spectrophotometric sensor 10 may be either a transmission or reflectance type sensor. Transmission type spectrophotometric sensors include an emitter 16 and a detector 18 that are typically placed on opposing sides of the sensor site. If the sensor site is a fingertip, for example, the spectrophotometric sensor 10 is positioned over the patient's fingertip such that the emitter 16 and the detector 18 lie on either side of the patient's nail bed. In other words, the spectrophotometric sensor 10 is positioned so that the emitter 16 is located on the patient's fingernail and the detector 18 is located 180° opposite the emitter 16 on the patient's finger pad. During operation, the emitter 16 shines one or more wavelengths of light through the patient's fingertip and the light received by the detector 18 is processed to determine various physiological characteristics of the patient. In each of the embodiments discussed herein, it should be understood that the locations of the emitter 16 and the detector 18 may be exchanged. For example, the detector 18 may be located at the top of the finger and the emitter 16 may be located underneath the finger. In either arrangement, the spectrophotometric sensor 10 will perform in substantially the same manner.

Reflectance type spectrophotometric sensors also operate by emitting light into the tissue and detecting the light that is transmitted and scattered by the tissue. However, reflectance type sensors include an emitter 16 and a detector 18 that are typically placed on the same side of the sensor site. For example, a reflectance type sensor may be placed on a patient's forehead or foot such that the emitter 16 and detector 18 lie side-by-side. Reflectance type spectrophotometric sensors detect light photons that are scattered back to the detector 18. A spectrophotometric sensor 10 may also be a transflectance sensor, such as a sensor that may subtend a portion of a baby's heel.

Figure 2A:
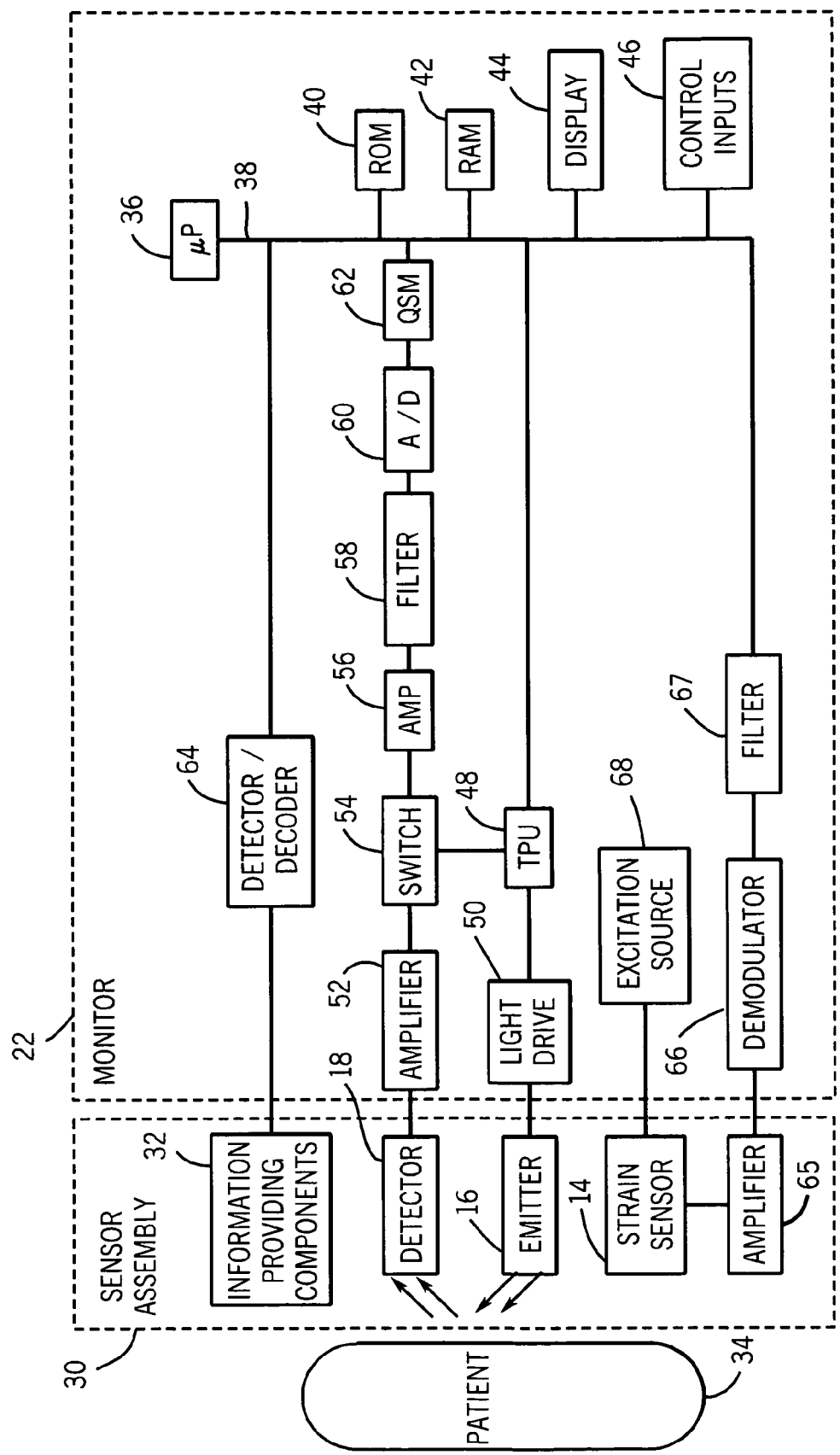
FIG. 2A is a block diagram of one embodiment of a system that may be configured to implement embodiments of the present technique.
Figure 2B:
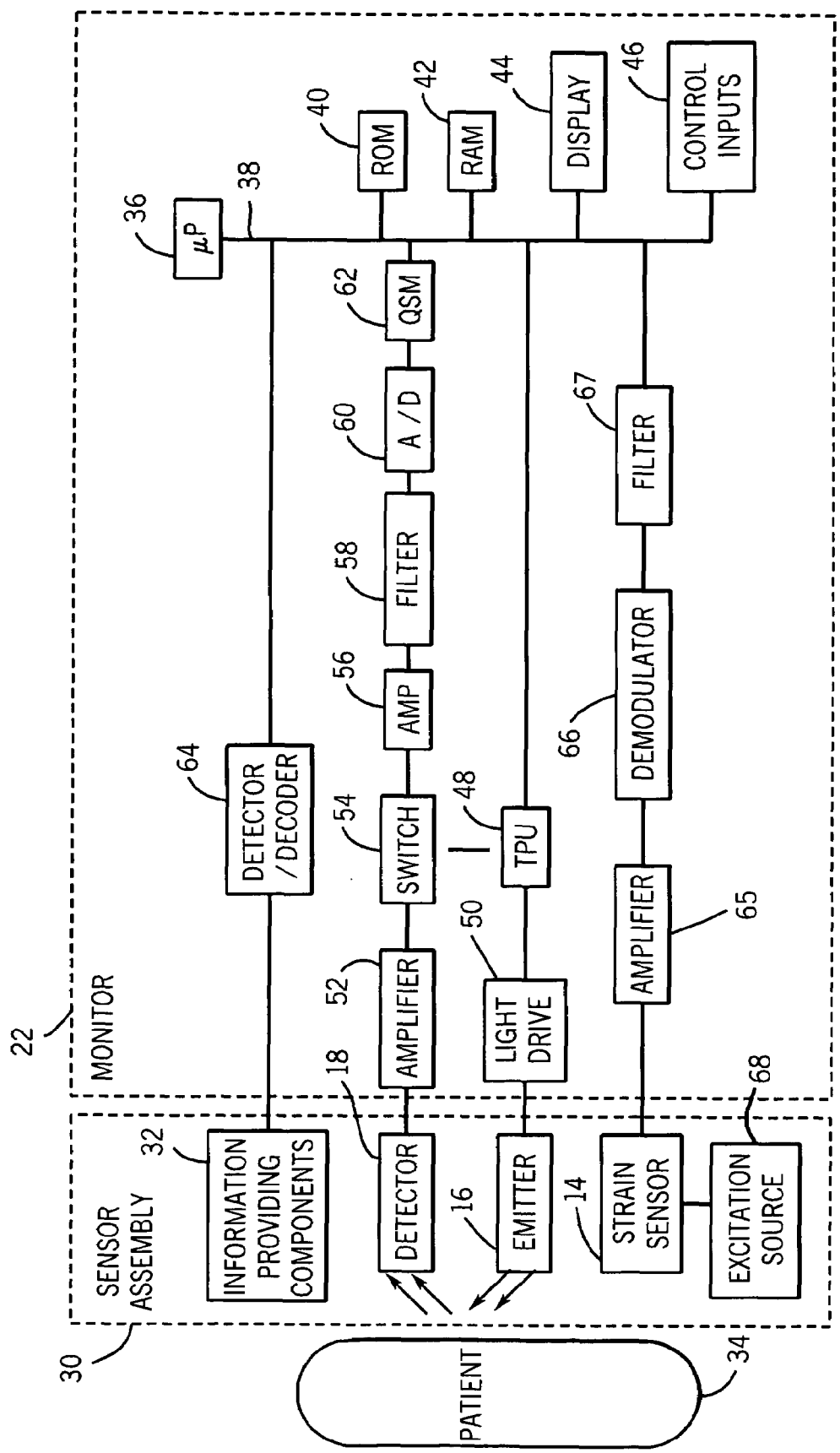
FIG. 2B is a block diagram of an alternative embodiment of a system that may be configured to implement other embodiments of the present technique.

FIGS. 2A and 2B are block diagrams of possible embodiments of the present invention. For simplicity, like reference numerals have been used to designate those features previously described in regard to FIG. 1. Turning now to FIG. 2A, a sensor assembly 30 is shown which may contain the strain sensor 14, the emitter 16, the detector 18 and one or more information providing components 32. The sensor assembly 30 may include the spectrophotometric sensor 10 alone or the spectrophotometric sensor 10 and the cable 20 together.

In one embodiment of the present invention, the information providing components 32 may provide signals to enable the monitor 22 to look up information needed for calculations and comparisons (such as information stored in the monitor 22). Information used in calculations may include, for example, coefficients needed to calculate blood-oxygen saturation, which could be looked up based on the wavelength of light from emitter 16. In addition, information about the expected strain sensor output for a given sensor assembly 30 may be looked up based on the type of spectrophotometric sensor 10 used. In another embodiment, the information providing components 32 may provide the monitor 22 with the necessary information directly. For instance, the expected strain sensor output for sensor assembly 30 may be provided to the monitor 22 by the information providing components 32 rather than being looked up from a table. The information providing components 32 may include resistors, memory chips or other memory media.

In one embodiment of the present technique, light from emitter 16 passes into blood perfused tissue of a patient 34 where it is scattered then detected by detector 18. The sensor assembly 30 may be configured to transmit signals from the detector 18 to the monitor 22. The monitor 22 may include a microprocessor 36 connected to an internal bus 38. Also connected to the bus are a read-only memory (ROM) 40, a random access memory (RAM) 42, a display 44 and one or more control inputs 46. A time processing unit (TPU) 48 provides timing control signals to light drive circuitry 50 which controls when the emitter 16 is illuminated, and if multiple light sources are used, the multiplexed timing for the different light sources. TPU 48 also controls the gating-in of signals from detector 18 through an amplifier 52 and a switching circuit 54. These signals are sampled at the proper time, depending upon which of multiple light sources is illuminated, if multiple light sources are used. Signals received from the detector 18 may be passed through an amplifier 56, a filter 58 and an analog-to-digital converter 60. The digital data is then stored in a queued serial module (QSM) 62, for later downloading to RAM 42 as QSM 62 fills up. In one embodiment, there may be multiple parallel paths of separate amplifier, filter and converter for multiple signals received.

Based on the value of the received signals corresponding to the light received by detector 18, microprocessor 36 may calculate the oxygen saturation using various algorithms. These algorithms require coefficients, which may be empirically determined corresponding to, for example, the wavelengths of light used. Information on the wavelengths used may be provided to the monitor 22 from the information providing components 32 or from separate information providing components from those shown. The signal from the information providing components 32 may pass to a detector/decoder 64, which may further process the signal, and/or may pass instructions to the microprocessor 36 to look up coefficient values. These values may be stored in a look up table in the ROM 40. In a two-wavelength system, the particular set of coefficients chosen for any pair of wavelength spectra is determined by the value indicated by the information providing components 32 corresponding to a particular light source in a particular sensor assembly 30. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 46. Control inputs 46 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

The monitor 22 may also be configured to receive signals from the sensor assembly 30 related to the strain sensor 14 that may be processed by the monitor 22 to determine when the spectrophotometric sensor 10 is misapplied. The strain sensor 14 may be made of any suitable material capable of providing an output indicative of the degree to which spectrophotometric sensor 10 is being bent. For example, strain sensor 14 may include a piezoresistive material, a piezoelectric material, a bonded metallic material or any other strain-sensitive material such that the resistance of the material changes based on the strain on the material. In the depicted exemplary embodiment, signals received from the strain sensor 14 are passed through an amplifier 65, a demodulator 66 and a low-pass filter 67. It should be appreciated by one skilled in the art that the amplifier 65 could be located in the sensor assembly 30 or in the monitor 22. For example, the amplifier 65 may be included in the sensor assembly 30 (e.g., integrated into the spectrophotometric sensor 10 or incorporated into the cable 20) as illustrated in FIG. 2A. Alternatively, the amplifier 65 may be located before the demodulator 66 in the monitor 22, as illustrated in FIG. 2B.

In an exemplary embodiment, the output waveform of excitation source 68 may be selected to reduce the noise in the output of amplifier 65 by minimizing the effects of thermoelectric potentials and of the 1/f noise and other noise characteristics of the amplifier 65. The excitation source 68 may be powered from any suitable source, such as a battery or wall outlet. To minimize coupling between the strain sensor 14 input and output and to minimize spurious radiation from the conductors carrying the excitation signal, a low-bandwidth excitation waveform may be used. Once again, it should be appreciated by one skilled in the art that this excitation source 68 could be located in the sensor assembly 30, as illustrated in FIG. 2A, or in the monitor 22, as illustrated in FIG. 2B. The combinations of amplifier 65 and excitation source 68 locations depicted are not the only possible combinations envisioned, but rather any combination may be possible. A demodulator 66 may convert the output signal from strain sensor 14 to a baseband signal. The demodulator 66 may be followed by a low-pass filter 67 to remove noise due to power-line frequency pickup, the amplifier, the operation of other apparatus applied to or in the vicinity of the patient, and all other sources of interfering signals. Bandpass filtering may also be employed in the amplifier 65 for the same purpose.

Further, the monitor 22 may be configured to receive information about the strain sensor 14 from a memory chip or other device, such as the information providing components 32. Such a device may include a code or other identification parameter that may allow the monitor 22 to select an appropriate software or hardware instruction for processing the signal. For example, the information providing components 32 may provide information regarding the strain sensor 14 and the spectrophotometric sensor 10 to the monitor 22 to allow the monitor 22 to determine if the observed strain sensor output is consistent with the proper usage of spectrophotometric sensor 10. In one embodiment, these information providing components 32 may be configured to notify the monitor 22 of the type of spectrophotometric sensor 10 being used (e.g., forehead or digit) so that an expected strain sensor output may be looked up from a table on the monitor. In another embodiment, the information providing components 32 may supply the expected strain sensor output to the monitor 22.

The signal from the information providing components 32 may pass to a detector/decoder 64, which may further process the signal, and/or may pass instructions to a microprocessor 36. Further, a monitor 22 may run an algorithm or code for processing the signal provided by the strain sensor 14. For example, in certain embodiments, the processing algorithm may receive information that compares the strain sensor output to that expected of a certain type of sensor, providing for a determination of misapplication of spectrophotometric sensor 10 depending on the parameters of the particular strain sensor 14. The monitor 22 may also be configured to provide an indication about the sensor condition, such as an audio alarm, visual alarm or a display message, such as "CHECK SENSOR." One embodiment of this process is described below, in reference to FIG. 4.

Figure 3A:
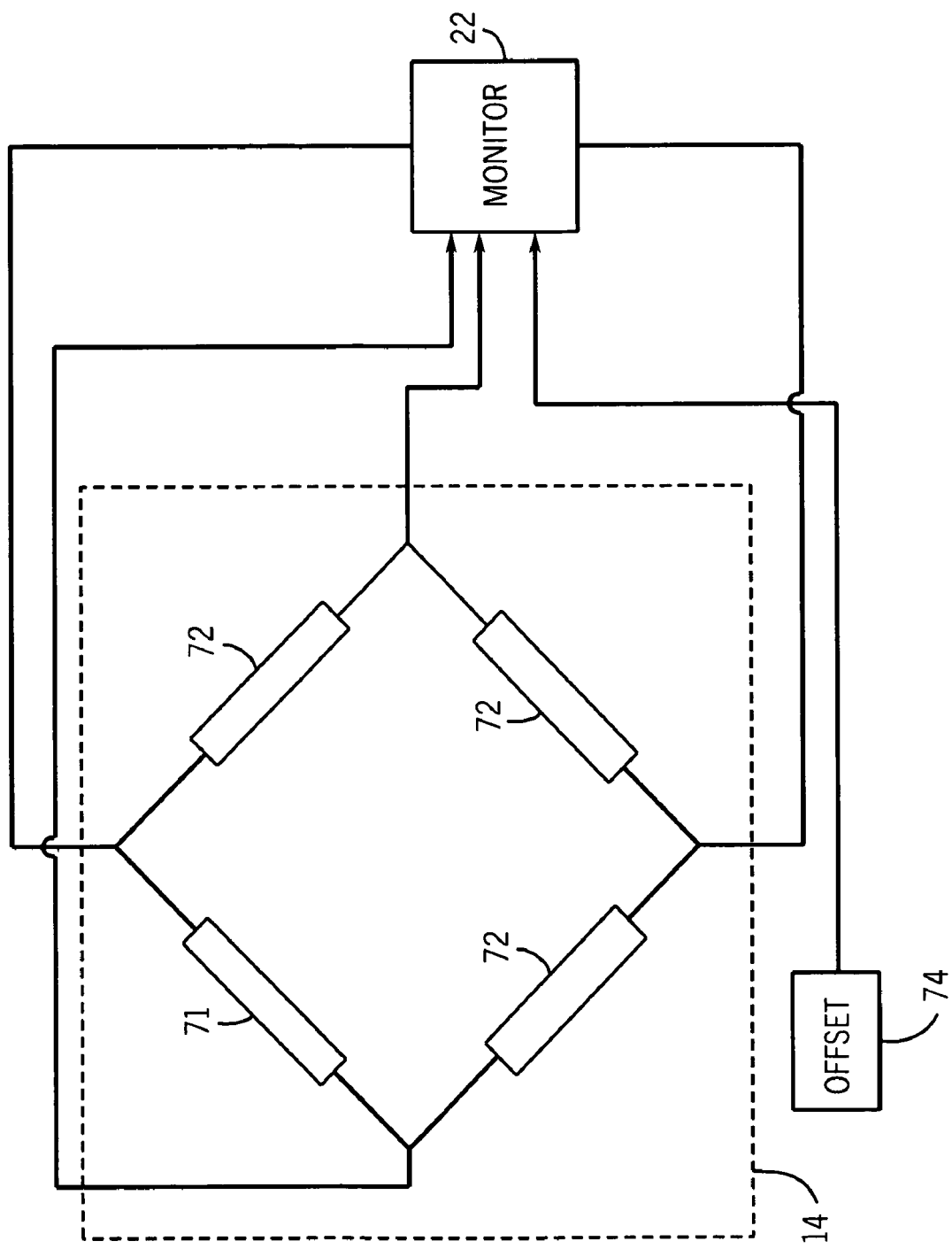
FIG. 3A is a block diagram of one embodiment of a strain sensor in accordance with aspects of the present technique.
Figure 3B:
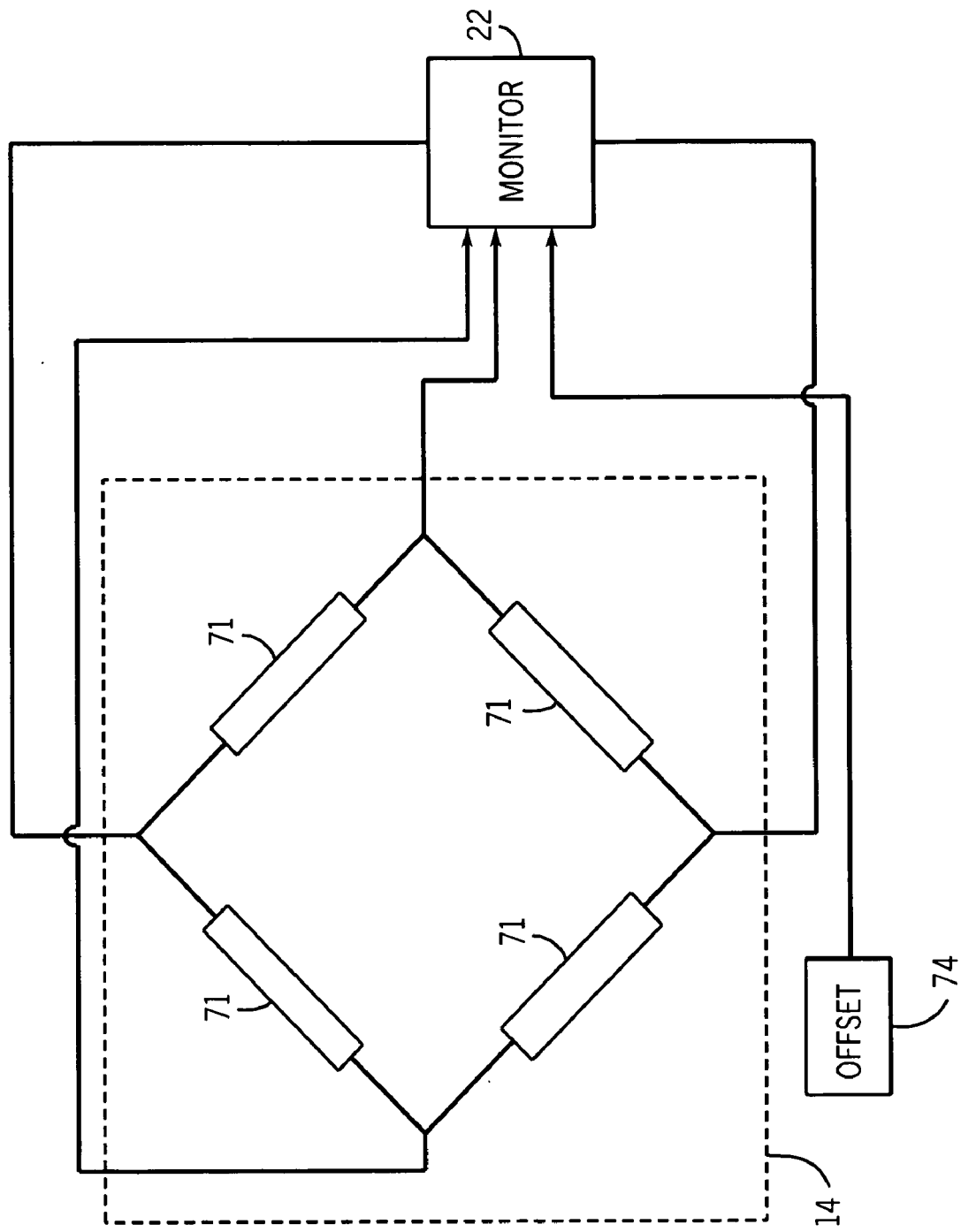
FIG. 3B is a block diagram of an alternative embodiment of a strain sensor in accordance with aspects of the present technique.

FIGS. 3A and 3B are block diagrams of possible embodiments of the strain sensor 14 that may be configured to implement the present technique. The strain sensor 14 may consist of a bridge including one or more strain sensing elements 71 with impedance that varies as a function of the mechanical strain in the element. Any or all of the strain sensing elements 71 may incorporate components that reduce the output in the zero-strain condition to an acceptable level. The strain sensor 14 may also include one or more resistors 72 to complete the bridge, depending on the number of strain sensing elements 71 used. FIG. 3A illustrates a strain sensor 14 in which only one strain sensing element 71 is used, while FIG. 3B illustrates a strain sensor 14 in which four strain sensing element 71 are used. As one skilled in the art will appreciate, the possible combinations of strain sensing elements 71 and resistors 72 are not limited to those shown but could be any combination in which at least one strain sensing element 71 is included in the bridge.

An offset element 74 (one possible information providing component 32) may be included in the sensor assembly 30 to provide information about the zero-strain offset output to the monitor 22, which may use this information to null out or otherwise account for the offset. As will be appreciated by those of ordinary skill in the art, the offset element 74 may also be provided in the monitor 22, though, for simplicity, it is depicted in FIGS. 3A and 3B as being a separate component. The interconnect assembly or assemblies may be constructed to minimize the pickup of all signals not due to the strain-induced output of the strain sensor 14, including cross-coupling between the bridge excitation and output signals.

Figure 4:
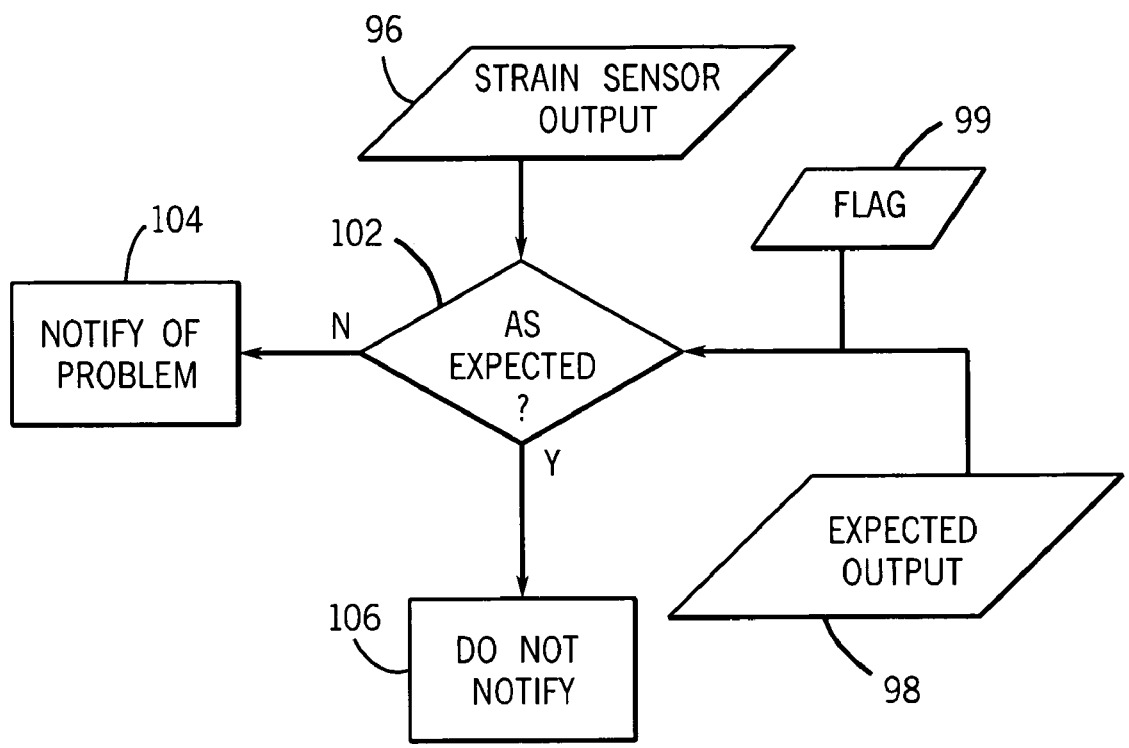
FIG. 4 is a flow chart of exemplary actions associated with determining whether a sensor is applied to the area for which it was designed in accordance with aspects of the present technique.

FIG. 4 is a flow chart of exemplary actions associated with determining whether the spectrophotometric sensor 10 is applied to the area for which it was designed. This determination may be made by comparing the strain sensor output 96 to an output threshold 98 for a spectrophotometric sensor of the type being used. A flag 99 indicates whether the output threshold 98 is a high or low threshold. The flag 99 indicates whether the strain sensor output 96 is expected to be above or below the threshold output 98 when the spectrophotometric sensor 10 is applied correctly. In one embodiment of the present invention, the output threshold 98 and flag 99 may be stored in the information providing components 32. In another embodiment of the present invention, information about the type of spectrophotometric sensor 10 and strain sensor 14 being used is provided by the information providing components 32 and the output threshold 98 and flag 99 are looked up from a table stored in the ROM 40.

The strain sensor output 96 and the output threshold 98 may then be compared (Block 102). For example, in one embodiment of the present technique the output threshold 98 may be determined by measuring the expected strain sensor output when a digit sensor is applied to a digit with the largest radius of curvature expected, and the flag 99 may be set to indicate that a strain sensor output 96 greater than the output threshold 98 is unacceptable. For example, in one implementation, the output threshold 98 may be set to 0.7 volts and the flag 99 may indicate that this is a high threshold. Therefore, if the strain sensor output 96 were 0.9 volts the threshold would be exceeded, and if the strain sensor output 96 were 0.6 volts the threshold would not be exceeded. As one skilled in the art will appreciate, the output threshold 98 and flag 99 may vary depending on the type of material used in the strain sensor 14. The threshold may be chosen to provide the desired degrees of correct identification of a misapplied sensor and incorrect identification of a properly applied sensor. If the strain sensor output 96 is not as expected, the monitor 22 may provide an indication (Block 104) about the sensor condition, such as an audible alarm, visual alarm or a display message, such as "CHECK SENSOR." Alternatively, the monitor 22 may cease display of the patient's physiological characteristics as an indication of incorrect spectrophotometric sensor placement. If the strain sensor output 96 is as expected, the monitor 22 may not indicate a sensor problem (Block 106).

Figure 5:
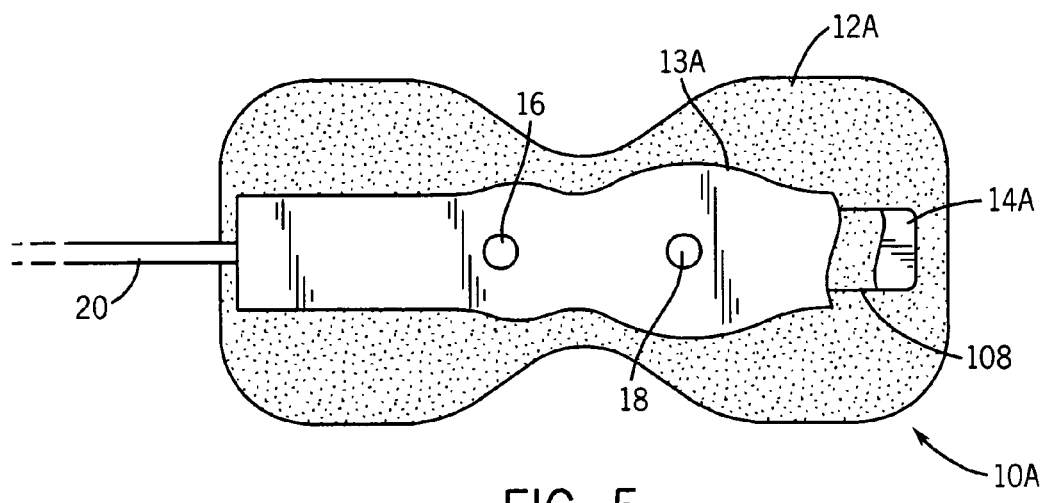
FIG. 5 is a cutaway view of a sensor assembly according to one embodiment of the present technique.
Figure 6:
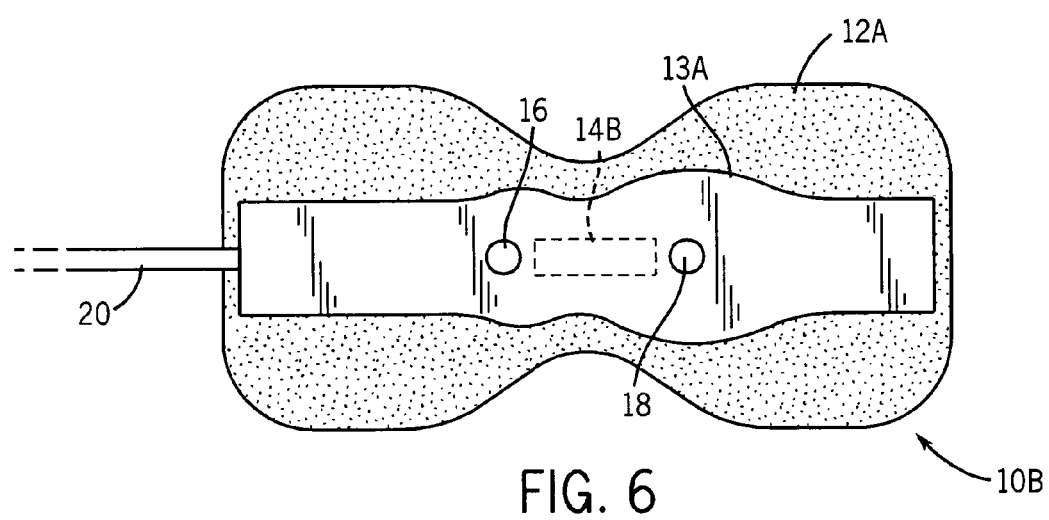
FIG. 6 is a plan view of a sensor assembly according to another embodiment of the present technique.
Figure 7:
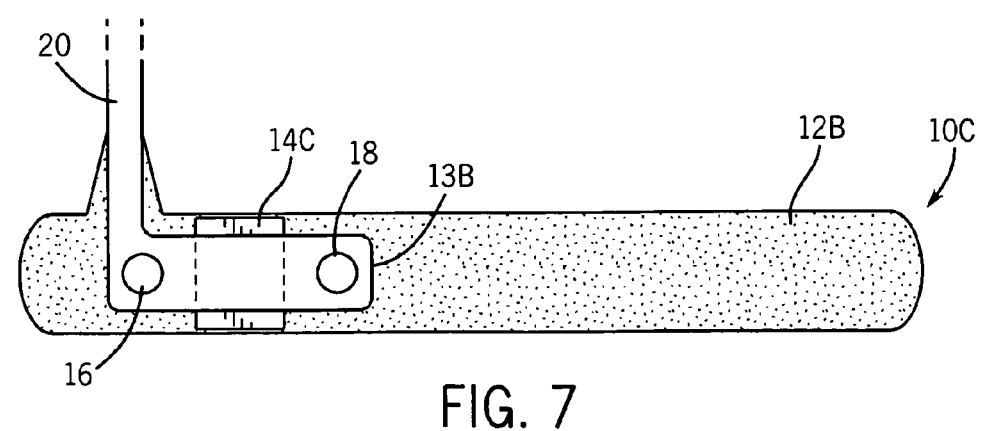
FIG. 7 is a plan view of a sensor assembly according to a further embodiment of the present technique.

FIGS. 5-7 illustrate spectrophotometric sensors 10 with various combinations of embodiments of sensor body 12, optical package 13 and strain sensor 14. The present technique is not intended to be limited to the combinations illustrated, but rather may include any combination of these embodiments or any other modifications, equivalents, and alternatives falling within the spirit and scope of the invention. Turning now to FIG. 5, a cutaway view of a spectrophotometric sensor 10A is shown according to one embodiment of the present technique. As described above in reference to FIG. 1, an optical package 13A may include the emitter 16 and the detector 18, and may be coupled to the cable 20. The optical package 13A may be attached to the strain sensor 14A via an adhesive layer 108 such that any bending of the optical package 13A results in a corresponding bend in a strain sensor 14A. The strain sensor 14A may run substantially the length of the optical package 13A or less and may also be coupled to the cable 20. The optical package 13A and strain sensor 14A may be disposed on a sensor body 12A, which may be configured for application to a particular area of the body, such as the forehead or digit.

FIG. 6 is a plan view of a spectrophotometric sensor 10B according to another embodiment of the present technique. The strain sensor 14B may be incorporated into the optical package 13A rather than being adhered to the exterior, as denoted by the dashed line. It should be appreciated that the strain sensor 14B may be located anywhere within the optical package 13A that would be expected to bend upon proper application of the spectrophotometric sensor 10B to the body area for which the spectrophotometric sensor 10B was designed. The strain sensor 14B may be configured such that it is as small as possible but still able to accurately provide a measurement related to the curvature of the optical package 13A.

FIG. 7 is a plan view of a spectrophotometric sensor 10C according to another embodiment of the present technique. The strain sensor 14C may be configured such that it is substantially perpendicular to an optical package 13B. It should be appreciated by one skilled in the art that the strain sensor 14C may be disposed at any angle relative to the optical package 13B as long as the strain sensor 14C generates a signal representative of the extent to which the spectrophotometric sensor 10 is bent or curved. The strain sensor 14C may be positioned completely under the optical package 13B or it may protrude from beneath the optical package 13B. In addition, the strain sensor 14C may be placed anywhere on the sensor body 12B that is expected to bend upon application of the spectrophotometric sensor 10C to the area of the body for which it was designed.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, intravascular dyes, and/or water content. Rather, the invention is to cover all modifications, equivalents, and alternatives falling within the spirit and scope of the invention as defined by the following appended claims.

What is claimed is:

1. A spectrophotometric sensor comprising:
  a sensor body;
  an emitter and a detector disposed on the sensor body; and
  a strain sensor disposed on the sensor body and positioned entirely between the emitter and the detector, wherein the strain sensor is capable of providing a signal indicative of sensor misapplication on a patient.

2. The spectrophotometric sensor of claim 1, wherein the spectrophotometric sensor comprises at least one of a pulse oximetry sensor or a tissue water sensor configured to measure a water fraction.

3. The spectrophotometric sensor of claim 1, wherein the signal comprises a measure of one of a voltage or a resistance.

4. The spectrophotometric sensor of claim 1, wherein the signal comprises a measure of an electrical property of the strain sensor.

5. The spectrophotometric sensor of claim 1, wherein the strain sensor comprises at least one of a piezoresistive material, a piezoelectric material or a bonded metallic material.

6. The spectrophotometric sensor of claim 1, wherein the strain sensor is adhered to an optical package containing the emitter and the detector.

7. The spectrophotometric sensor of claim 1, wherein the strain sensor is disposed within an optical package containing the emitter and the detector.

8. The spectrophotometric sensor of claim 1, comprising an information providing component comprising at least a threshold signal value for the strain sensor.

9. The spectrophotometric sensor of claim 1, comprising an information providing component comprising at least identification information that may be utilized by a monitor to determine at least a threshold signal value for the strain sensor.

10. A system comprising:
  a spectrophotometric sensor comprising:
    a sensor body;
    an emitter and a detector disposed on the sensor body; and
    a strain sensor disposed on the sensor body, wherein the strain sensor is configured to provide a signal related to a curvature of the spectrophotometric sensor; and
  a monitor adapted to be operatively coupled to the sensor, the monitor being capable of determining whether the spectrophotometric sensor is applied to a sensor site for which it is designed based on the signal from the strain sensor.

11. The system of claim 10, wherein the monitor comprises a pulse oximetry monitor.

12. The system of claim 10, wherein the monitor is configured to compare the signal with a threshold signal value.

13. The system of claim 12, wherein the monitor is configured to determine whether the threshold signal value is a high threshold or a low threshold based on a signal flag.

14. The system of claim 12, wherein the monitor is configured to provide a notification when the comparison of the signal with the threshold signal value indicates that the spectrophotometric sensor is not applied to the sensor site for which it is designed.

15. The system of claim 10, wherein the monitor is configured to look up a threshold signal value based on information received from an information providing component of the spectrophotometric sensor.

16. The system of claim 10, wherein the monitor is configured to receive a threshold signal value from an information providing component of the spectrophotometric sensor.

17. A method of manufacturing a sensor, comprising:
  providing an optical package in which an emitter and a detector are disposed;
  combining the optical package and a strain sensor such that a signal related to a curvature of the optical package can be measured, wherein the strain sensor is positioned entirely between the emitter and the detector; and
  disposing the strain sensor and the optical package on a sensor body.

18. The method of claim 17, wherein combining the strain sensor and the optical package comprises adhering the strain sensor to the optical package.

19. The method of claim 17, wherein combining the strain sensor and the optical package comprises integrating the strain sensor into the optical package.

20. The method of claim 17, wherein the strain sensor comprises at least one of a piezoresistive material, a piezoelectric material or a bonded metallic material.

21. A method for detecting a misapplied sensor, comprising:
  receiving a signal related to a curvature of a spectrophotometric sensor at a monitor;
  comparing the signal with a threshold signal value; and
  providing a notification at or from the monitor if the comparison indicates that the spectrophotometric sensor is misapplied.

22. The method of claim 21, wherein the threshold signal value depends on the body area to which the spectrophotometric sensor is configured to be applied.

23. The method of claim 21, wherein providing a notification at or from the monitor comprises at least one of sounding an audible alarm, displaying a message, or ceasing display of one or more physiological characteristics measured by the spectrophotometric sensor.

* * * * *